(12) United States Patent
Sato et al.

(10) Patent No.: US 9,360,562 B2
(45) Date of Patent: Jun. 7, 2016

(54) RADIATION IMAGING APPARATUS AND RADIATION IMAGING SYSTEM

(71) Applicant: CANON KABUSHIKI KAISHA, Tokyo (JP)

(72) Inventors: Sho Sato, Saitama (JP); Toshio Kameshima, Kumagaya (JP); Tomoyuki Yagi, Honjo (JP); Katsuro Takenaka, Honjo (JP); Hideyuki Okada, Honjo (JP); Atsushi Iwashita, Honjo (JP); Eriko Sugawara, Honjo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 146 days.

(21) Appl. No.: 13/974,118

(22) Filed: Aug. 23, 2013

(65) Prior Publication Data
US 2014/0061492 A1    Mar. 6, 2014

(30) Foreign Application Priority Data

Aug. 31, 2012   (JP) .................................. 2012-192455

(51) Int. Cl.
*G01J 1/42*        (2006.01)
*G01T 1/00*        (2006.01)
(Continued)

(52) U.S. Cl.
CPC .................. *G01T 1/17* (2013.01); *A61B 6/4233* (2013.01); *A61B 6/542* (2013.01); *A61B 6/544* (2013.01); *H04N 5/32* (2013.01)

(58) Field of Classification Search
CPC ..................................... G01T 1/16; G01T 1/17

USPC ..................................... 250/393, 394, 370.08
See application file for complete search history.

(56) References Cited

U.S. PATENT DOCUMENTS 6,208,710 B1    3/2001  Nagai
2003/0086523 A1  5/2003  Tashiro et al.
(Continued)

FOREIGN PATENT DOCUMENTS

CN      102313896 A    1/2012
JP      H11-151233 A   6/1999
(Continued)

OTHER PUBLICATIONS

Extended European search report issued on Dec. 6, 2013, in counterpart Application No. 13181959.1.
(Continued)

*Primary Examiner* — David Porta
*Assistant Examiner* — Meenakshi Sahu
(74) *Attorney, Agent, or Firm* — Carter, DeLuca, Farrell & Schmidt LLP

(57) ABSTRACT

To provide a radiation imaging apparatus and a radiation imaging system that can detect radiation with high accuracy, the radiation imaging apparatus includes: a detection unit in which conversion elements that convert radiation into an electric signal are arranged in a matrix shape; a radiation detection unit configured to detect an irradiation state of radiation; a drive circuit configured to drive the detection unit in accordance with the irradiation state detected by the radiation detection unit; and a radiographing kind setting unit configured to set a radiographing kind, wherein the radiation detection unit changes a radiation detection capability in accordance with the radiographing kind set by the radiographing kind setting unit.

20 Claims, 14 Drawing Sheets

(51) Int. Cl.
*G01T 1/17* (2006.01)
*A61B 6/00* (2006.01)
*H04N 5/32* (2006.01)

(56) References Cited

U.S. PATENT DOCUMENTS

2008/0054182 A1* 3/2008 Yokoyama et al. ...... 250/370.09
2012/0001079 A1* 1/2012 Okada ........................ 250/366
2012/0132825 A1 5/2012 Amitani et al.

FOREIGN PATENT DOCUMENTS

JP 2010-268171 A 11/2010
WO 2011/008421 A1 1/2011

OTHER PUBLICATIONS

Chinese Office Action issued in corresponding application No. 201310376842.2 on Feb. 28, 2015.

* cited by examiner

FIG. 5

| RADIOGRAPHING SITE | BUILD OF SUBJECT | X-RAY INPUT RATIO | GAIN |
|---|---|---|---|
| CHEST SIDE | SLENDER | 30 | 33 |
| | FAT | 10 | 100 |
| HEAD | SLENDER | 80 | 12 |
| | FAT | 60 | 17 |
| HAND | --- | 100 | 10 |

$$\text{GAIN SETTING} \propto \frac{1}{\text{X-RAY INPUT AMOUNT}}$$

FIG. 10A
CHEST FRONT
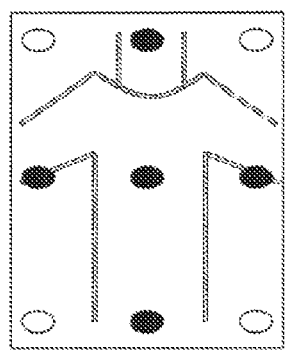
FIG. 10B
CHEST SIDE
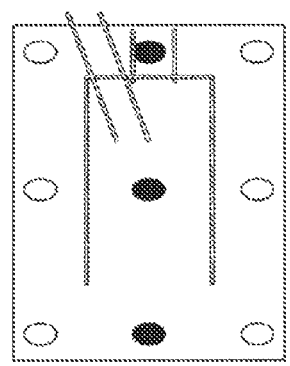
○ GAIN: Lo
● GAIN: Hi
FIG. 11
| RADIOGRAPHING SITE | BUILD OF SUBJECT | X-RAY INPUT RATIO | GAIN |
|---|---|---|---|
| CHEST SIDE | SLENDER | 30 | 33 |
|  | FAT | 10 | 100 |
| HEAD | SLENDER | 80 | 12 |
|  | FAT | 60 | 17 |
| HAND | --- | 100 | 10 |
| DIRECT TRANSMISSION | --- | 1000 | 1 |
$$\text{GAIN SETTING} \propto \frac{1}{\text{X-RAY INPUT AMOUNT}}$$

RADIATION IMAGING APPARATUS AND RADIATION IMAGING SYSTEM

BACKGROUND OF THE INVENTION

1. Field of the Invention

The present invention relates to a radiation imaging apparatus and a radiation imaging system.

2. Description of the Related Art

In recent years, imaging apparatuses including a flat panel detector (hereinafter abbreviated as "FPD") formed of a semiconductor material, have started to be put to practical use as imaging apparatuses that used for medical diagnostic imaging or a nondestructive inspection using an X-ray. In an FPD, a plurality of pixels having conversion elements constructed using semiconductor material such as a-Si that is capable of converting radiation into electric charges and switching elements that transfer electric signals that correspond to the electric charges are arranged two-dimensionally. Such imaging apparatuses including an FPD are used, for example, in medical diagnostic imaging as digital imaging apparatuses for still image radiographing like general radiographing or moving image radiographing such as fluoroscopic radiographing.

When performing radiographing, a radiation imaging apparatus performs radiographing in synchrony with the operations of an X-ray generating apparatus. As synchronization methods, for example, a unit is available in which the X-ray generating apparatus and the radiation imaging apparatus are synchronized electrically connecting the two apparatuses to each other, or a unit is available in which the radiation imaging apparatus is synchronized with the X-ray generating apparatus by detecting X-ray that is radiated from the X-ray generating apparatus. In the former case, because service personnel connect the X-ray generating apparatus and the radiation imaging apparatus with a cable, the connection work involves time and labor, and furthermore the X-ray generating apparatus and the radiation imaging apparatus must be fixed and used as a single pair of apparatuses. In the latter case, a method is known in which an X-ray detector is provided inside and outside the radiation imaging apparatus, or in which the radiation imaging apparatus itself performs detection of radiation, and in this case there is the advantage that time and labor for connection work is not required and the radiation imaging apparatus is portable and can be used in combination with various X-ray generating apparatuses.

Normally, in an FPD, pixels that include a photoelectric conversion element and a switching element are two-dimensionally arrayed, and reading of signals from the photoelectric conversion elements and resetting of the photoelectric conversion elements is performed in row units. Before X-ray is irradiated, the switching elements are subjected to on/off control in row units, and a dark current component flowing to the photoelectric conversion elements is reset ("initializing operation"). If an X-ray irradiation signal is input or X-ray is detected during an initializing operation, it is necessary to immediately end the reset operation and transition to an accumulation operation. If a transition is not made to the accumulation operation even though an X-ray irradiation signal has been input, a time lag will arise between the time that the user pushed the exposure button and the actual photographed image, and an unintended image in which a difference in level or the like arises will be obtained. Further, if an initializing operation is continued even though X-ray was detected, since X-ray signals that are generated at the photoelectric conversion elements will be reset, unnecessary X-ray will have been irradiated at the subject and the amount of radiation exposure may increase.

Japanese Patent Application Laid-Open. No. H11-151233 discloses technology that includes a radiation detection unit and that immediately shifts the operating state from a radiographing preparation state an accumulation state when the start of radiation irradiation is determined. Further, Japanese Patent Application Laid-Open No. 2010-268171 discloses a radiation image radiographing apparatus that detects a current that flows through a bias line that supplies a bias voltage to a radiation detecting element, detects the start irradiation of radiation based on a value of the current that is detected, and holds an electric charge that is generated inside the radiation detecting element.

However, in Japanese Patent Application Laid-Open No. H11-151233 and Japanese Patent Application Laid-Open No. 2010-268171, in some cases it is not possible for the radiation detection unit to adapt to various radiographing kinds (the radiographing site and the build of a subject, a moving image or a still image radiographing mode, and the like). In diagnostic imaging using X-ray, X-ray irradiation conditions differ depending on the kind of radiographing. Therefore, a radiation detection unit is demanded that is capable of accurately detecting irradiation of X-ray with respect to various irradiation conditions.

SUMMARY OF THE INVENTION

An object of the present invention is to provide a radiation imaging apparatus and a radiation imaging system that are capable of highly accurate radiation detection.

The present invention provides a radiation imaging apparatus comprising: a detection unit in which conversion elements that convert radiation into an electric signal are arranged in a matrix shape; a radiation detection unit configured to detect an irradiation state of radiation; a drive circuit configured to drive the detection unit in accordance with the irradiation state detected by the radiation detection unit; and a radiographing kind setting unit configured to set a radiographing kind, wherein the radiation detection unit changes a radiation detection capability in accordance with the radiographing kind set by the radiographing kind setting unit.

Radiation detection can be performed accurately with respect to various radiographing kinds. The radiographing kinds include, for example, the radiographing site and the build of a subject, and a moving image or still image radiographing mode.

Further features of the present invention will become apparent from the following description of exemplary embodiments with reference to the attached drawings.

BRIEF DESCRIPTION OF THE DRAWINGS

FIG. 5 is a view illustrating an example of a gain setting table according to radiographing kinds.

FIGS. 10A and 10B are views for describing detection capability setting.

FIG. 11 is a view illustrating an example of a detection capability setting table.

DESCRIPTION OF THE EMBODIMENTS

Preferred embodiments of the present invention will now be described in detail in accordance with the accompanying drawings.

First Embodiment

Figure 1:
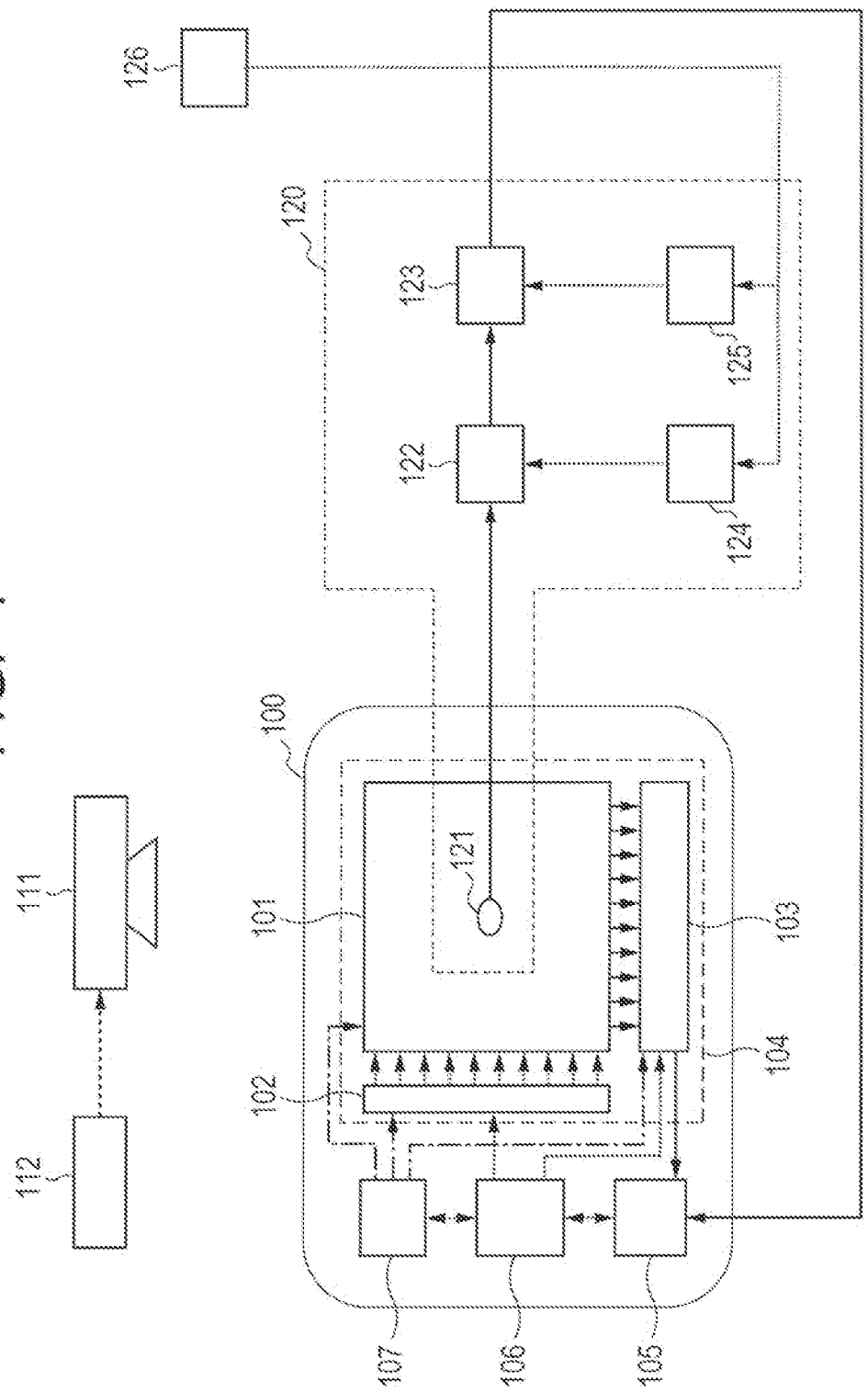
FIG. 1 is a view that illustrates a configuration example of a radiation imaging system according to a first embodiment.

FIG. 1 is a block diagram illustrating a configuration example of a radiation imaging system according to a first embodiment of the present invention. The radiation imaging system includes a radiation generating apparatus and a radiation imaging apparatus. The imaging apparatus 100 includes a detector (FPD) 104 having a detection unit 101 including a plurality of pixels that convert radiation into electric signals, a drive circuit 102 that drives the detection unit 101, and a read circuit 103 that outputs electric signals from the detection unit 101 as image data. The imaging apparatus 100 further includes a signal processing unit 105 that processes the image data from the FPD 104 and that outputs the resulting data, a control unit 106 that controls operations of the FPD 104 by supplying respective control signals to each of the components, and a power supply unit 107 that supplies a bias to each of the components, respectively. The signal processing unit 105 inputs a control signal transmitted from an unshown control computer, and provides the control, signal to the control unit 106. The signal processing unit 105 also inputs information regarding the potential of a signal line that is transmitted from the read circuit 103 during a period in which radiation is irradiated, and transmits the information to the control computer. The power supply unit 107 includes a power supply circuit such as a regulator that inputs a voltage transmitted from an unshown external power supply or internal battery, and that supplies required voltages to the detection unit 101, the drive circuit 102, and the read circuit 103. The radiation generating apparatus 111 irradiates radiation in accordance with radiation irradiation conditions that are received as instructions from the control console 112. The imaging apparatus 100 and the radiation generating apparatus 111 are not electrically connected and there is no exchange of signals therebetween. The radiation detection unit 120 includes a radiation detection sensor 121 that detects a radiation irradiation state, a current detecting unit 122 that detects a current from the radiation detection sensor 121, a gain setting unit 124, a comparison unit 123, and a threshold setting unit 125 that sets a threshold of the comparison unit 123. The user uses the radiographing kind setting unit 126 to set a radiographing kind (a radiographing site and a build of the subject, a moving image or a still image radiographing mode or the like) prior to radiographing. The gain setting unit 124 sets a gain of the current detecting unit 122 in accordance with the radiographing kind that was set by the radiographing kind setting unit 126. The comparison unit 123 compares a voltage signal from the current detecting unit 122. The threshold setting unit 125 sets a threshold voltage of the comparison unit 123 in accordance with the radiographing kind that was set by the radiographing kind setting unit 126. Although the radiation detection sensors 121 are arranged on a radiation irradiation face of the detection unit 101 according to the present embodiment, the radiation detection sensors 121 may be arranged on the opposite side of the radiation irradiation face. Further, to enable reliable detection of radiation irradiation even if a radiation irradiation region is narrowed, the radiation detection sensor 121 is desirably arranged at a center part in the detection unit 101. According to the present embodiment, a direct-type sensor that converts radiation directly into an electric signal or a sensor formed by coating a fluorescent substance that converts radiation into visible rays on an Si photodiode may be used as the radiation detection sensor 12. However, the present invention is not limited to such sensors, and the radiation detection sensor may be a component that includes one part of wiring included in the detection unit 101 and obtains a signal that detects a radiation irradiation state from a predetermined region of the detection unit 101.

Figure 2:
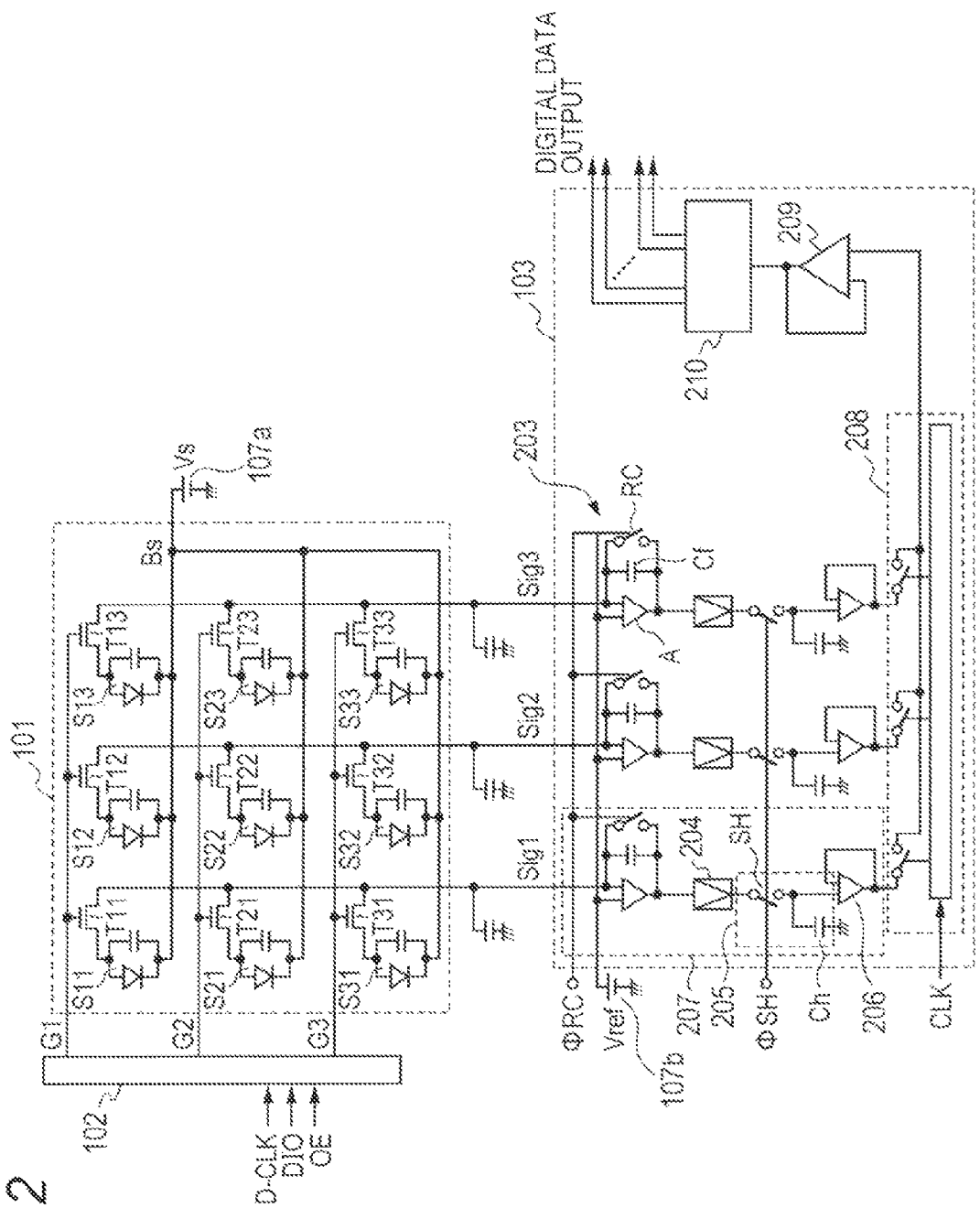
FIG. 2 is a view that illustrates a configuration example of a radiation imaging apparatus according to the first embodiment.

FIG. 2 is a view that illustrates a configuration example of an imaging apparatus 100 according to the first embodiment of the present invention. Elements in FIG. 2 having the same configuration as that described with reference to FIG. 1 are assigned the same reference numerals, and detailed descriptions thereof are omitted. Further, in FIG. 2, an imaging apparatus including a detection unit 101 having pixels of three rows by three columns is illustrated for ease of description. In actuality, however, an imaging apparatus has a larger number of pixels. For example, a 17-inch imaging apparatus has pixels of approximately 2800 rows by approximately 2800 columns. The detection unit 101 has a plurality of pixels arranged in a matrix. In the present embodiment, each of the pixels has conversion elements S11 to S33 that convert radiation into an electric charge (electric signal), and switching elements T11 to T33 that outputs an electric signal corresponding to the electric signal. In the present embodiment, a metal-insulator-semiconductor (MIS)-type photosensor that is provided on an insulating substrate such as a glass substrate and that includes amorphous silicon as the main material is used as a photoelectric conversion element which converts light into an electric charge. An indirect-type conversion element having a wavelength, converter that is provided on the side on which radiation is incident of the above-described photoelectric conversion element and that converts radiation into light falling within the band of wavelengths that can be sensed by the photoelectric conversion element, or a direct-type conversion element that directly converts radiation into an electric charge is suitably used as the conversion element. A transistor having a control terminal and two main terminals is suitably used as the switching elements T11 to T33. In the present embodiment, a thin film transistor (TFT) is used. One of the electrodes of the conversion elements S11 to S33 is electrically connected to one of the two main terminals of the switching elements T11 to T33, and the other electrode is electrically connected to a bias power supply 107a via a common bias line Bs. A plurality of switch elements in the row direction, for example, switching elements T11 to T13, have control terminals that are commonly electrically connected to a drive line G1 of the first row, and drive signals for controlling the conductive state of the switching elements are applied from the drive circuit 102 via drive lines on a row-by-row basis. In a plurality of switching elements in the column direction, for example, switching elements T11 to T31, the other main terminals thereof are electrically connected to a signal line Sig1 of the first column. Electric signals corresponding to the electric charge of the conversion elements S11 to S31 are output to the read circuit 103 via signal lines Sig1 during a period in which the switching elements T11 to T31 are in a conductive state. A plurality of signal lines Sig1 to Sig3 arranged in the column direction carry she electric signals output from the plurality of pixels to the read circuit 103 in parallel. Although each of the pixels described in the present embodiment includes the conversion elements S11 to S33 and the switching elements T11 to T33, the present embodiment is not limited thereto. The present embodiment also includes a pixel that further includes at least an amplification transistor between the signal lines Sig1 to Sig3 or conversion elements S11 to S33 and the switching elements T11 to T33. Further, a configuration may be adopted that includes a pixel that further includes an initialization transistor that initializes the conversion elements S11 to S33 or a node provided between the conversion elements S11 to S33 and the amplification transistor.

The read circuit 103 includes a plurality of amplifier circuits 207 that amplify the electric signals output in parallel from the detection unit 101, that are provided in correspondence with the respective signal lines. Further, each amplifier circuit 207 includes an integrating amplifier 203 that amplifies an output electric signal, a variable amplifier 204 that amplifies an electric signal from the integrating amplifier 203, a sample and hold circuit 205 that samples and holds the amplified electric signal, and a buffer amplifier 206. The integrating amplifier 203 has an operational amplifier A that amplifies a read electric signal and that outputs the amplified signal, an integrating capacitor Cf, and a reset switch RC. The integrating amplifier 203 includes a mechanism that is capable of changing an amplification factor by changing the value of the integrating capacitor Cf. An output electric signal is input to an inverting input terminal of the operational amplifier A from the detection unit 101, a reference voltage Vref is input from a reference power supply 107b a non-inverting input terminal of the operational amplifier A, and an amplified electric signal is output from an output terminal of the operational amplifier A. Further, the integrating capacitor Cf is arranged between the inverting input terminal and the output terminal of the operational amplifier A. The sample and hold circuit 205 is provided in correspondence with each variable amplifiers 204, and is constituted by a sampling switch SH and a sampling capacitor Ch. Further, the read circuit 103 includes a multiplexer 208 that sequentially outputs electric signals read in parallel from the respective amplifier circuits 207 and that outputs the electric signals as serial image signals, and a buffer amplifier 209 that performs impedance conversion on the image signals and outputs the converted image signals. An image signal bout that is an analog electric signal output from the buffer amplifier 209 is converted into digital image data by an A/D converter 210 and is then output to the signal processing unit 105 (FIG. 1). Image data that is processed by the signal processing unit 105 is output to the control computer.

The drive circuit 102 outputs drive signals having a conductive voltage boom for bringing switching elements T11 to T33 into a conductive state and a non-conductive voltage Vss for bringing the switching elements T11 to T33 into a non-conductive state in accordance with control signals D-CLK, GE, DIO input from the control unit 106 (FIG. 1) to the respective drive lines G1 to G3. Thus, the drive circuit 102 controls the conductive state and the non-conductive state of the switching elements T11 to T33, and drives the detection unit 101. When the start of irradiation of radiation is detected by the radiation detection unit 120, the drive circuit 102 makes the operating state of the detection unit 101 transition from a standby state to an accumulation state. Further, when the end of irradiation of radiation is detected by the radiation detection unit 120, the drive circuit 102 makes the operating state of the detection unit 101 transition from the accumulation state to a read state.

The power supply unit 107 illustrated in FIG. 1 includes the bias power supply 107a and the reference power supply 107b of the amplifier circuits 207 that are illustrated in FIG. 2. The bias power supply 107a commonly supplies a bias voltage Vs to the other electrode of each conversion elements S11 to S33 via the bias line Bs. The reference power supply 107b supplies the reference voltage Vref to the non-inverting input, terminal of each operational amplifier A.

The control unit 106 illustrated in FIG. 1 controls the operation of the FED 104 by inputting a control signal from the control computer or the like outside the apparatus via the signal processing unit 105 and supplying various control signals to the drive circuit 102, the power supply unit 107, and the read circuit 103. The control unit 106 illustrated in FIG. 1 controls the operation of the drive circuit 102 illustrated in FIG. 2 by supplying a control signal D-CLK, a control signal GE, and a control signal DIG to the drive circuit 102. Here, the control signal D-CLK is a shift clock of a shift register used as a drive circuit 102, the control signal DIO is a pulse that is transferred by the shift register, and control signal OE is a signal that controls an output terminal of the shift register. Further, the control unit 106 controls the operations of the respective components of the read circuit 103 by supplying a control signal ΦRC, a control signal ΦSH, and a control signal CLK to the read circuit 103 illustrated in FIG. 2. Here, the control signal ΦRC controls the operations of the reset switches RC of the integrating amplifiers 203, the control signal ΦSH controls the operations of the switch SH of the sample and hold circuit 205, and the control signal CLK controls the operation of the multiplexer 208.

Figure 3:
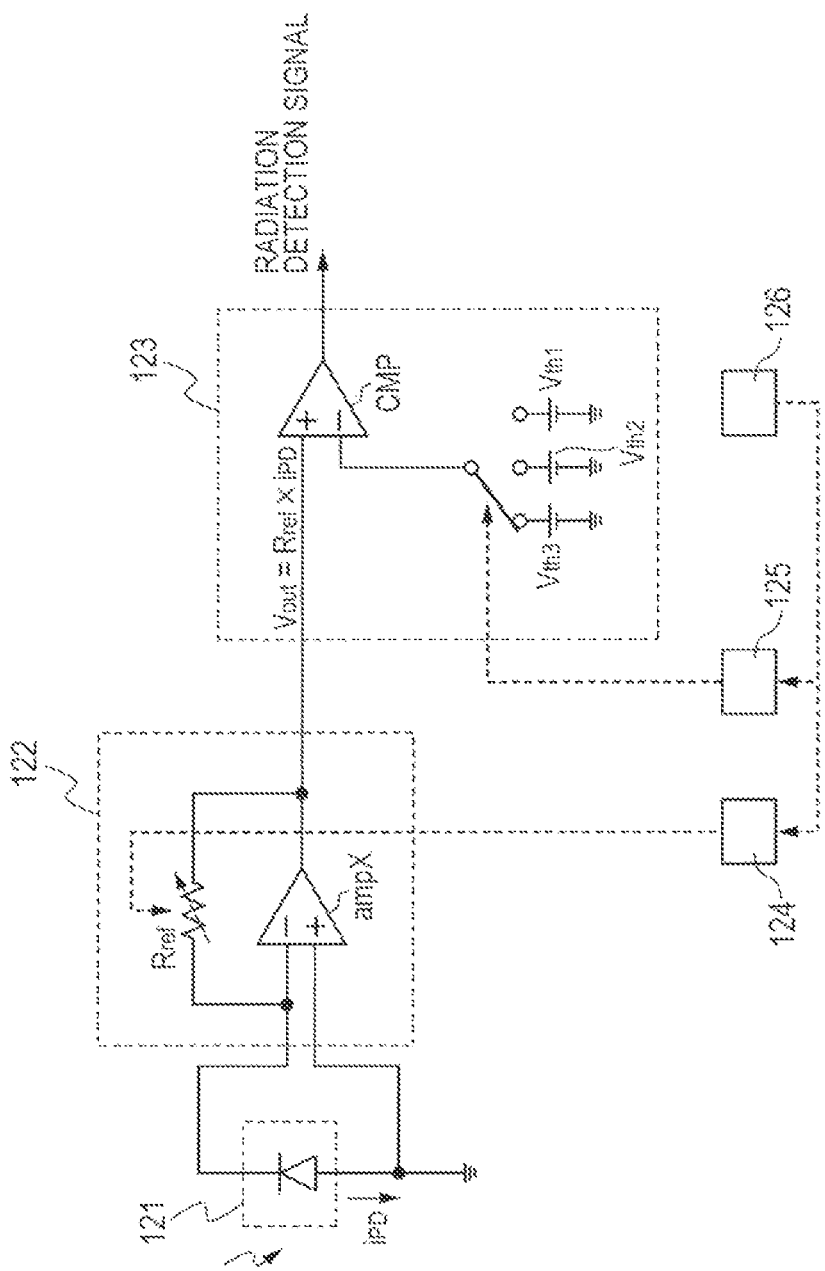
FIG. 3 is an equivalent circuit diagram of a radiation detection unit.
Figure 4:
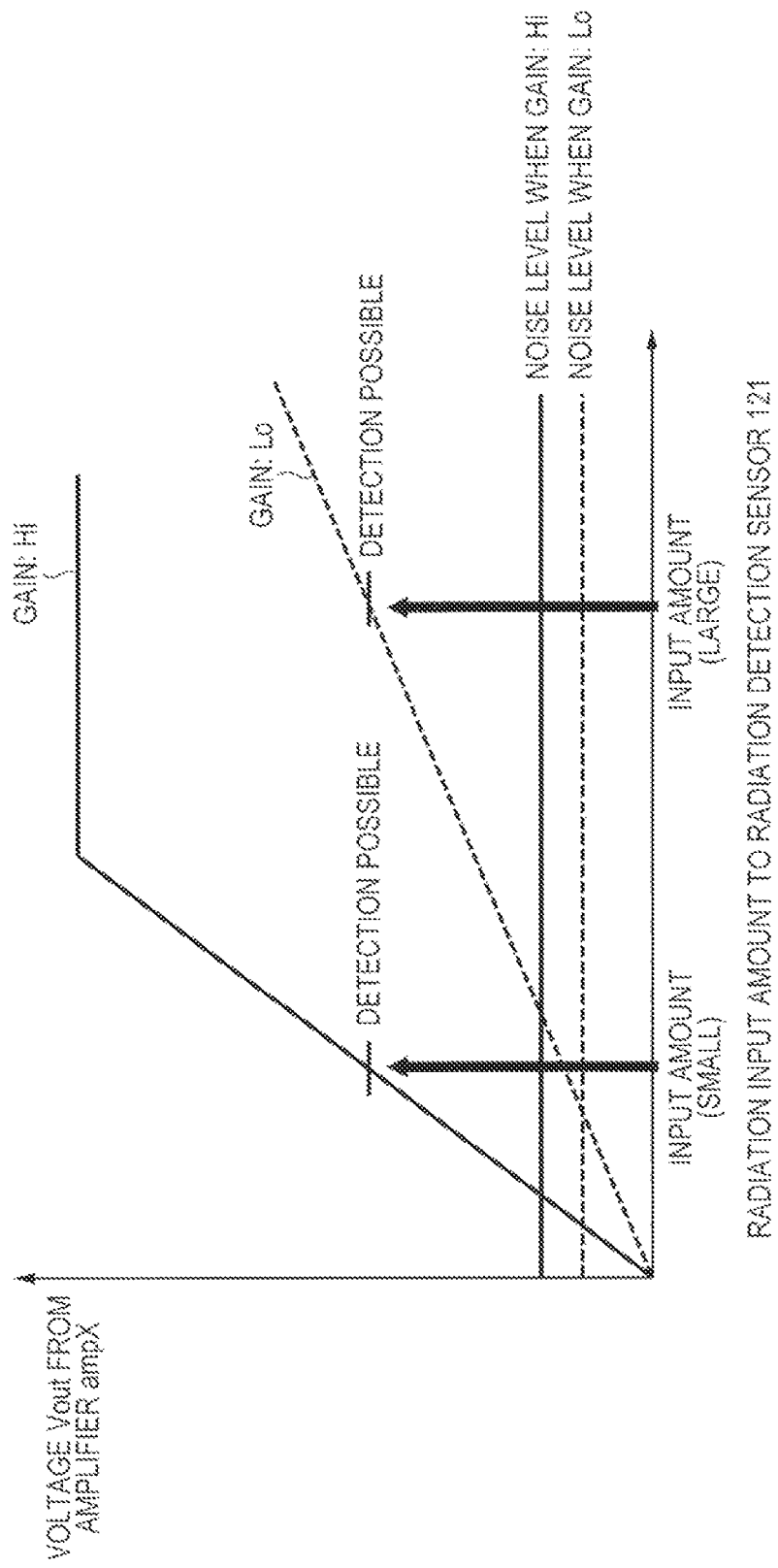
FIG. 4 is a view for describing gain setting at a gain setting unit.
Figure 6:
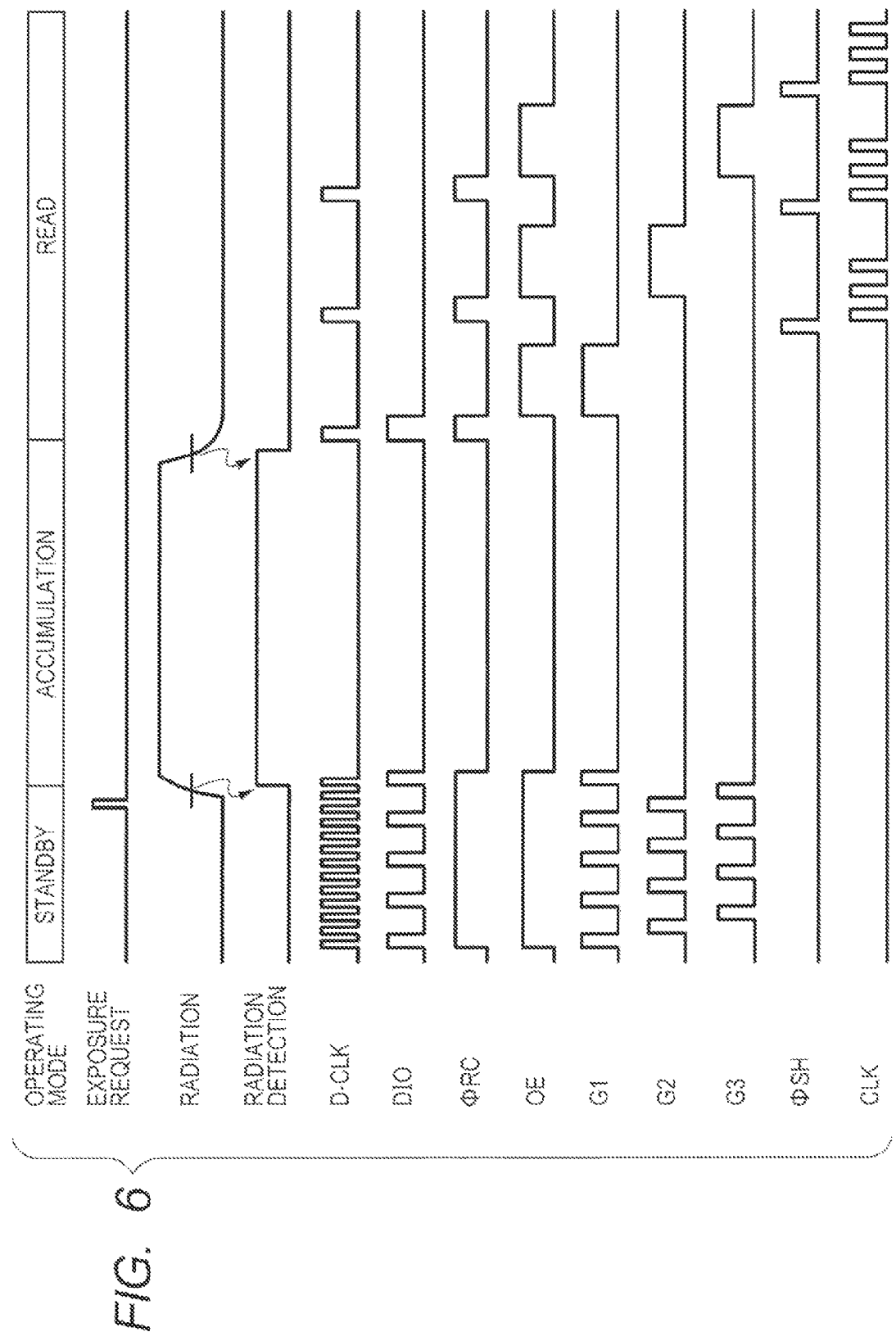
FIG. 6 is a timing chart of a radiation imaging apparatus.

Next, the operations of the radiation imaging system will be described with reference to FIGS. 1 to 6. FIG. 3 is an equivalent circuit diagram of the radiation detection unit 120. FIG. 4 is a view for describing gain setting at the gain setting unit 124. FIG. 5 is a view illustrating an example of a gain setting table according to radiographing kinds. FIG. 6 is a timing chart of the radiation imaging apparatus.

When performing radiographic radiographing, first the operator sets the radiographing kind by means of the radiographing kind setting unit 126. Here, the term "radiographing kind" refers to a radiographing site and a build of the subject, or a radiographing mode such as a still image or a moving image radiographing mode. Since the radiation irradiation conditions or irradiation regions will differ depending on the radiographing kind, it is necessary for the operator to set the radiographing kind in advance before radiographing.

Next, when the power of the imaging apparatus 100 is turned on and a bias voltage Vs is supplied to the conversion elements S11 to S33, the imaging apparatus 100 starts a standby operation (FIG. 6). In the standby operation, an initializing operation is repeatedly performed to reset a dark current that flows though the conversion elements S11 to S33. In the initializing operation, the integrating capacitor Cf of the integrating amplifiers 203 and the signal lines Sig1 to Sig3 are reset by the reset switch RC. Further, in synchrony with the control signal. DIO and the control signal D-CLK that are sent to the drive circuit 102, the conductive voltage Vcom is applied to the drive line G1 to place the switching elements T11 to T13 of she pixels in the first row in a conductive state. The conversion elements S11 to S13 are reset as a result of the switching elements T11 to T13 entering a conductive state. The conversion elements S11 to S33 of all the pixels are reset by repeatedly performing control of the conductive state of the switching elements and resetting in this manner in sequence for the second row and third row. To continue the initializing operation, the control signal DIO is again output to the drive circuit 102, and the conductive voltage Vcom is applied to the drive line G1 of the first row. The initializing operation is repeatedly performed in the above described manner while the imaging apparatus 100 is in the standby operation.

When an exposure request signal is transmitted to the radiation generating apparatus 111 as a result of an operation by the operator at the control console 112, radiation irradiation is started immediately. When radiation is irradiated onto the imaging apparatus 100, the radiation detection unit 120 detects the radiation and outputs a radiation detection signal to the signal processing unit 105. In addition, the signal processing unit 105 sends a signal to the control unit 106 to stop the initializing operation and transition to an accumulation operation. As a result, the imaging apparatus 100 transitions to the accumulation operation (FIG. 6). During the accumulation operation, the non-conductive voltage Vss is applied to the switching elements T11 to T33 so that the switching elements T11 to T33 of all pixels enter a non-conductive state.

Thereafter, when the radiation irradiation ends, the end of irradiation of radiation is detected by the radiation detection unit 120, and the signal of the end of irradiation of radiation is output to the signal processing unit 105. Next, the signal processing unit 105 sends a signal to the control unit 106 to transition from the accumulation operation to a read operation. As a result, the imaging apparatus 100 transitions to a read operation (FIG. 6). In the read operation, first the integrating capacitors Cf and the signal lines Sig1 to Sig3 are reset by the reset switch RC. Next, the conductive voltage Vcom is applied to the drive line G1 from the drive circuit 102 to place the switching elements T11 to T13 in the first row in a conductive state. As a result, electric signals based on electric charges generated in the conversion elements S11 to S13 in the first row are output to the respective signal lines Sig1 to Sig3. The electric signals that are output in parallel via the respective signal lines Sig1 to Sig3 are amplified by the integrating amplifier 203 and variable amplifier 204 of each amplifier circuit 207, respectively. The respective electric signals amplified are held in parallel in the sample and hold circuits 205 of the respective amplifier circuits 207 by operating the switch SH of the sample and hold circuit 205 in response to the control signal ΦSH. After holding the signals, the integrating capacitors Cf and signal lines Sig1 to Sig3 are reset. After resetting, similarly to the operations performed for the first row, the conductive voltage Vcom is applied to the drive line G2 of the second row, and the switching elements T21 to T23 of the second row are placed in a conductive state. In the period, in which the switching elements T21 to T23 of the second row are in the conductive state, the multiplexer 208 sequentially outputs the electric signals that are held in the sample and hold circuit 205. As a result, the electric signals from the pixels in the first row that were read in parallel are converted into serial image signals and output, and the A/D converter 210 converts the serial image signals into image data for one row and outputs the image data. By performing the above described operations in row units from the first row to the third row, image data for one frame is output from the imaging apparatus. As described above, the control unit 106 and the drive circuit 102 drive the detection unit 101 and the read circuit 103 in accordance with an irradiation state that is detected by the radiation detection unit 120.

FIG. 3 is a view that illustrates a configuration example of the radiation detection unit 120 in FIG. 1. When radiation is irradiated at the radiation detection sensor 121, the radiation detection sensor 121 converts to a current iPD that corresponds to an input amount of irradiated radiation. In addition, the current iPD also flows to a feedback resistance Rref of the current detecting unit 122, an is subjected to current-voltage conversion by the amplifier ampX. Here, a voltage Vout that is output from the amplifier ampX is expressed as Rref×iPD. Further, a voltage value that is output from the amplifier ampX can be controlled by changing the resistance value of the feedback resistance Rref, and the feedback resistance Rref becomes the gain of the amplifier ampX. The voltage Vout is input to a comparator CMP of the comparison unit 123 and compared with any threshold voltage Vth among arbitrary threshold voltages Vth1 to Vth3. In a case where radiation is irradiated and a current flows to the radiation detection sensor 121 and the voltage Vout from the amplifier ampX exceeds the threshold voltage Vth, the comparator CMP outputs a radiation detection signal (high level logic) indicating the start of irradiation of radiation. Subsequently, as described above, the radiation detection signal is output to the signal processing unit 105, and the imaging apparatus 100 transitions to an accumulation operation. Thereafter, when irradiation of radiation ends, the voltage Vout from the amplifier ampX is less than the threshold voltage Vth, and the comparator CMP outputs a radiation detection signal (low-level logic) indicating the end of irradiation of radiation. The signal processing unit 105 then outputs a signal to the control unit 106 so that the imaging apparatus 100 transitions to a read operation.

A feature of the present embodiment is that the gain of the current detecting unit 122 and the threshold voltage Vth of the comparison unit 123 can be changed in accordance with a radiographing kind that is set by an operator. In this case, the value of the feedback resistance Pref of the current detecting unit 122 is set so that an output voltage Vout of the amplifier ampX remains within a dynamic range in which the amplifier ampX operates normally. Normally, based on the relation Vout=Rref×iPD, the resistance value of the feedback resistance Rref is set so that the Vout is a value from several tens of millivolts (mV) to several volts (V). A value of approximately $10^5 \Omega$ to $10^9 \Omega$ is used as the feedback resistance Pref.

Next, a method of setting the gain of the current detecting unit 122 and of setting the threshold voltage Vth of the comparison unit 123 is described. The radiation detection sensor 121 detects radiation that was transmitted through a subject. The conditions of radiation irradiation differ depending on the radiographing site and build of the subject or the radiographing mode such as a still image or a moving image radiographing mode. Consequently, a radiation amount that is input to the radiation detection sensor 121 differs according to the kind of radiographing. Therefore, according no the present embodiment, the most suitable gain setting is performed for various radiographing kinds.

As described above, the start of irradiation of radiation is detected by detecting that the voltage Vout from the amplifier ampX exceeds the threshold voltage Vth. The detection performance of the radiation detection unit 120 depends on the following points.

Noise
Time response
SN ratio

Here, the term "noise" refers to, for example, a dark current of the radiation detection sensor 121, thermal noise of the feedback resistance. Rref, an input offset current of the amplifier ampX, and an input offset voltage of the comparator CMP and the like. In the radiation detection unit 120 illustrated in FIG. 3, as a characteristic of these kinds of noise, a dark current of the radiation detection sensor 121 or an input offset current of the amplifier ampX is amplified in proportion to a gain. In contrast, thermal noise of the feedback resistance Rref or an input offset voltage of the comparator CMP is not amplified in proportion to a gain. That is, the noise of the radiation detection unit 120 includes noise that is amplified in proportion to a gain and noise that is not amplified in proportion to a gain. Therefore, the entire amount of the noise of the radiation detection unit 120 is not amplified in proportion to the gain.

FIG. 4 illustrates two kinds of input-output characteristics for a case where a gain setting of the current detecting unit 122 is low and a case where the gain setting is high. In a case where the input amount is small, if the gain setting is low, the proportion of the noise level, with respect to the output voltage Vout from the amplifier ampX is large. That is, the SN ratio is small. In contrast, if the gain setting is high, the proportion of the noise level is small. That is, the SN ratio is large. Accordingly, by setting the gain to a high value, the SN ratio at the radiation detection unit 120 can be raised. Here, the term "SN ratio" refers to a ratio obtained by dividing the output voltage Vout from the amplifier ampX by the sum total of the noise.

However, when the gain is set to a high value, a time constant RC value of the amplifier ampX increases, and the time response of the output voltage Vout more deteriorates. Consequently, there is a possibility that a time period from when radiation is actually irradiated until the radiation irradiation is detected at the radiation detection unit 120 will increase. Further, when detecting the end of radiation also, there is a possibility that a time period from when radiation irradiation is actually ended until the end of radiation irradiation is detected will increase.

According to the present embodiment, in a case where the radiation input amount to the radiation detection sensor 121 is small, the gain setting is set to a high value to raise the SN ratio. That is, the resistance value of the feedback resistance Rref is made a large value. As a result, even in a case where a radiation input amount to the radiation detection sensor 121 is small, erroneous detection due to noise can be prevented. On the other hand, in a case where a radiation input amount to the radiation detection sensor 121 is large, the gain setting is lowered. Since a radiation input amount is large, the SN ratio is large. There is a low possibility of occurrence of erroneous detection, and therefore it is not necessary to set the gain to a high value. Further, if the gain is unnecessarily set to a high value, the time response deteriorates and leads to the aforementioned adverse effects.

FIG. 5 is a view that illustrates an example of a gain setting table according to radiographing kinds in actual radiographing, as shown in the table, radiation irradiation conditions are determined depending on the radiographing site and build of the subject. Consequently, utilizing the data, the gain setting unit 124 sets a resistance value of the feedback resistance Rref of the amplifier ampX in accordance with a radiographing kind that is set in advance with the radiographing kind setting unit 126 before radiographing. The resistance value is set by means of a signal from the gain setting unit 124. It is desirable for the resistance value of the feedback resistance Ref to be set so as to be in inverse proportion to the radiation input amount.

The threshold voltage Vth of the comparison unit 123 changes according to the gain setting. As described above, in a case where the gain is set to a high value, since the amount of noise that is superimposed on the voltage Vout from the amplifier ampX is large, the threshold voltage Vth is set to a high value. Further, in a case where the gain is sec to a low value, since the amount of noise that is superimposed on the voltage Vout from the amplifier ampX is small, the threshold voltage Vth is set to a low value. The lower the threshold voltage Vth is, the shorter the time that is taken for the radiation detection unit 120 to detect the radiation irradiation after the radiation is irradiated. Therefore, it is desirable to set the threshold voltage Vth as low as possible. The threshold voltage Vth is set to any one of the threshold voltages Vth1 to Vth3 by means of a signal from the threshold setting unit 125. By setting the optimal gain and threshold voltage Vth in accordance with the radiographing kind in this manner, a radiation imaging apparatus can be realized in which the occurrence of erroneous detection is reduced and irradiation of radiation is detected with high accuracy.

Figure 7:
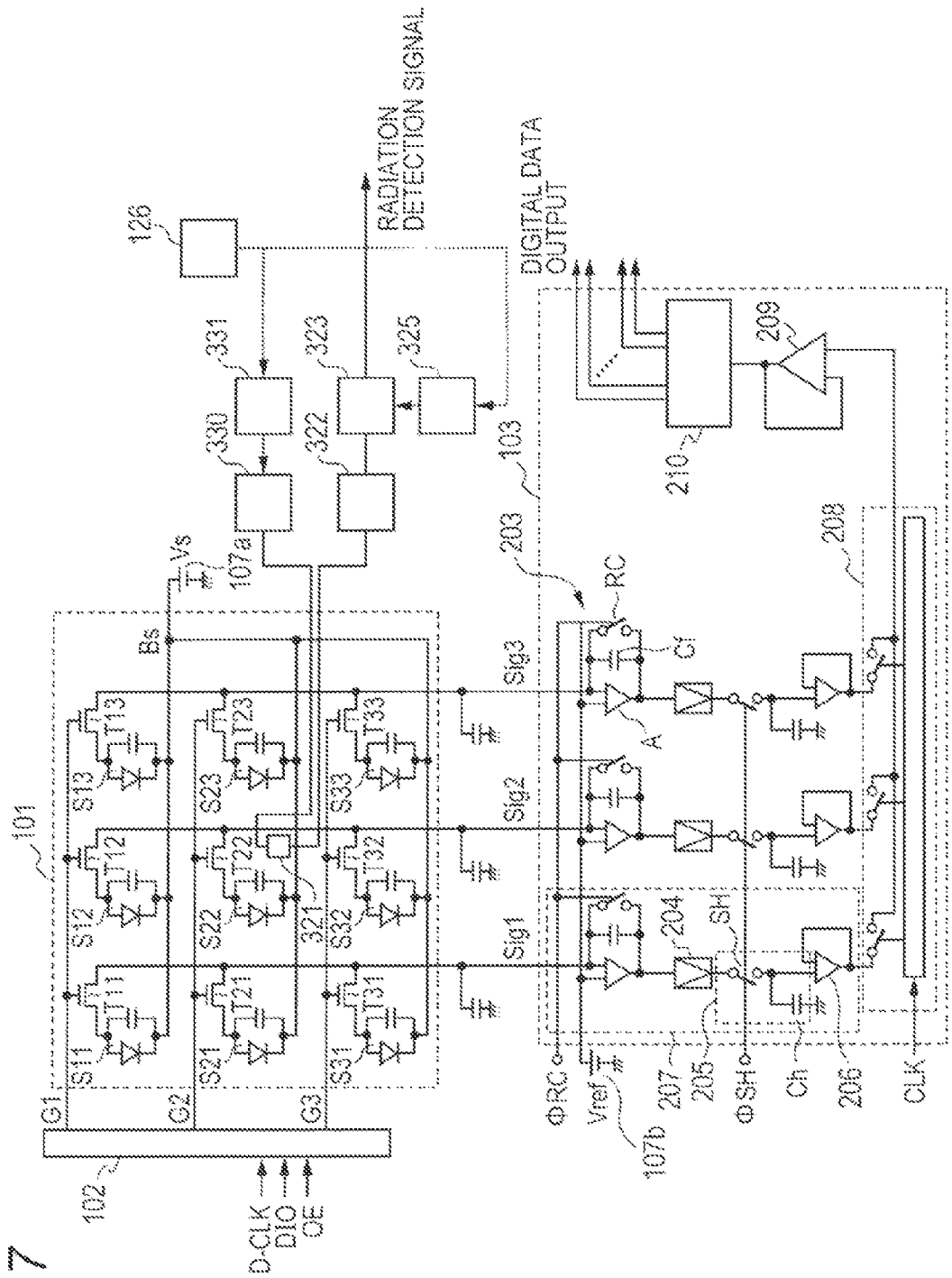
FIG. 7 is a view illustrating another configuration example of a radiation imaging apparatus.
Figure 8:
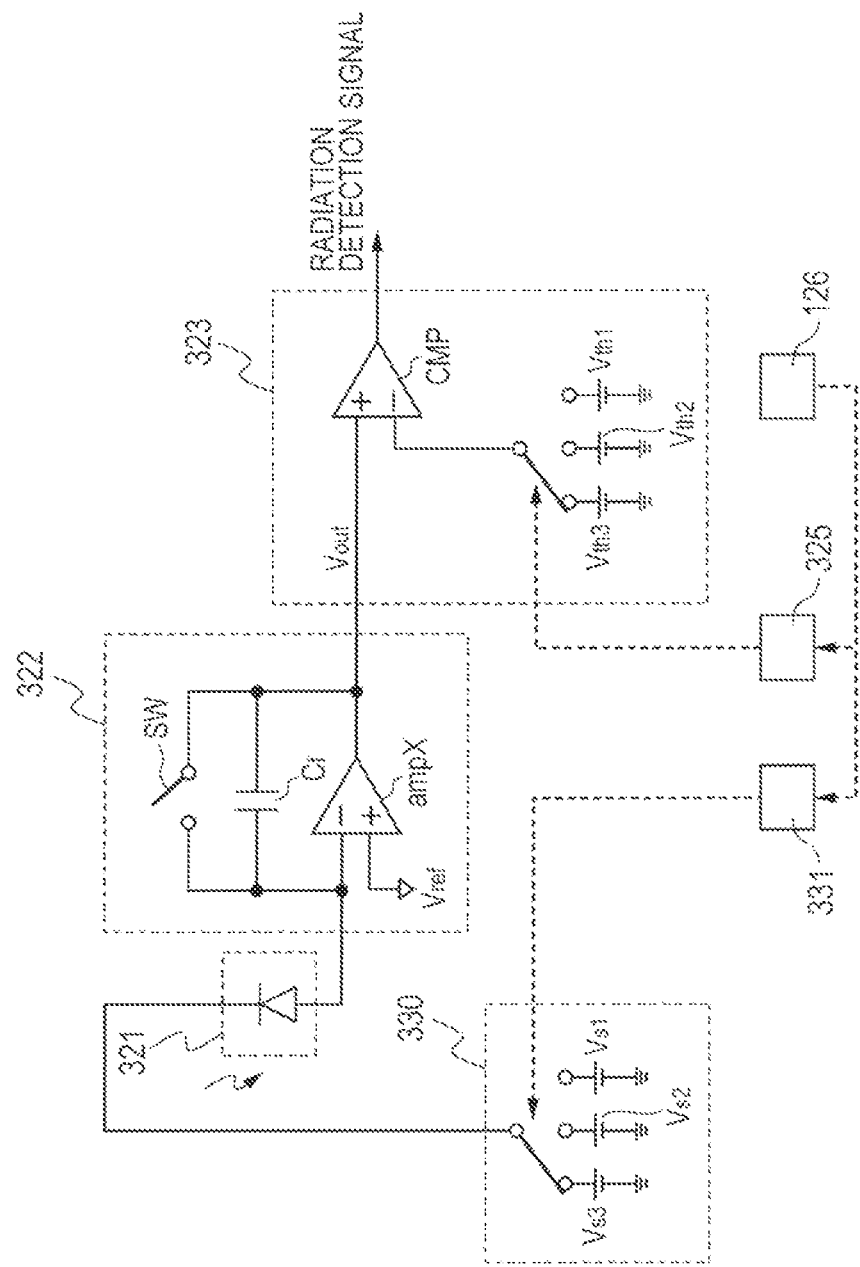
FIG. 8 is an equivalent circuit diagram of a radiation detection unit in a case where a radiation detecting pixel is used.

FIG. 7 is a view that illustrates a configuration example of another radiation imaging apparatus. Although, as described above, irradiation of radiation is detected using the radiation detection sensor 121 in the present embodiment, a configuration may also be adopted in which a pair of radiation detecting pixels 321 that includes two adjacent radiation detecting pixels 321 is separately provided in the detection unit 101. FIG. 8 is an equivalent circuit diagram of a radiation detection unit in the case of using the radiation detecting pixel 321. The radiation detection unit includes a voltage detecting unit 322, a comparison unit 323, a threshold setting unit 325, a bias switching unit 330, and a bias setting unit 331. The radiation detecting pixel 321 includes an MIS sensor that was made using a-Si. In a case where the radiation detecting pixel 321 is provided in the detection unit 101, instead of the above described gain setting of the current detecting unit 122, the sensitivity of the radiation detecting pixel 321 is set. The sensitivity of the radiation detecting pixel 321 is set by means of a bias voltage value VS. The bias setting unit 331 controls the bias switching unit 330 in accordance with the radiographing kind that was set by the radiographing kind setting unit 126. The bias voltage value VS is set to any one of bias voltages Vs1 to Vs3 by the bias switching unit 330, and is supplied to the radiation detecting pixel 321. In a sensor made using a-Si, there are a large number of trap levels produced by dangling bonds because the sensor is a non-crystalline semiconductor. Accordingly, the movement of electrons and holes caused by traps becomes active depending on the electric field intensity inside the semiconductor, and the sensitivity can be changed by the bias voltage value VS.

When radiation is irradiated on the radiation detecting pixel 321, a photocharge is generated and is accumulated in a feedback capacitor Cf of the voltage detecting unit (integrating circuit) 322. An output voltage signal Vout that corresponds to the accumulated charge is input to the comparator CMP of the comparison unit 123. If the output voltage Vout exceeds the threshold voltage Vth, the comparator CMP outputs the radiation detection signal. When radiation detection ends, a switch SW of the voltage detecting unit 322 is turned on and the radiation detecting pixel 321 is refreshed.

According to this detection method also, when a radiation input amount to the radiation detecting pixel 321 is small, the sensitivity is set to a high value (bias voltage value VS is set to a large value), and when a radiation input amount to the radiation detecting pixel 321 is large, the sensitivity is set to a low value (bias voltage value VS is set to a small value).

Further, in the present embodiment, radiation irradiation may also be detected by detecting a current that flows in the bias line Bs of the detection unit 101. In such case, the aforementioned radiation detection unit 120 is connected to the bias line Bs of the detection unit 101.

Second Embodiment

Figure 9:
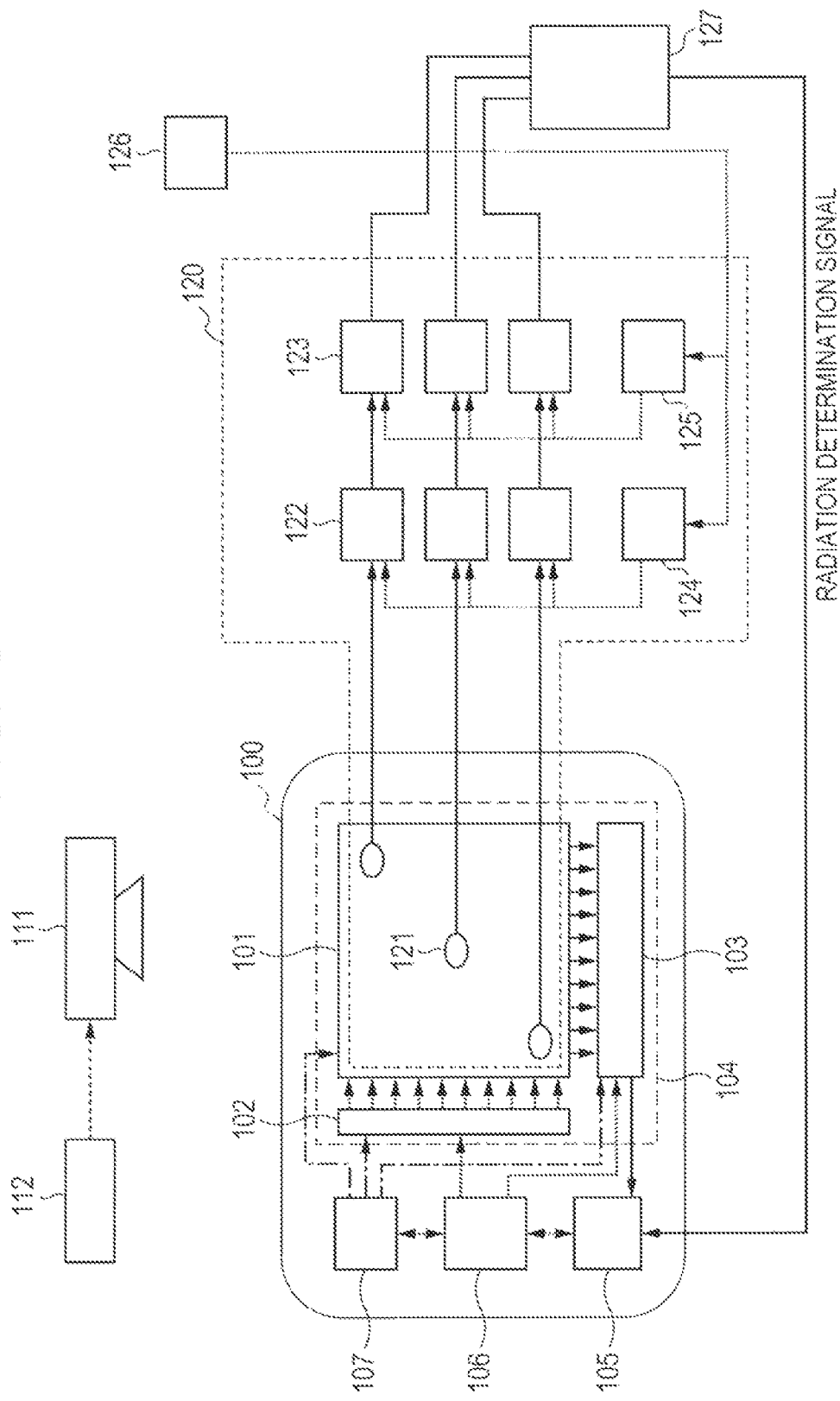
FIG. 9 is a view that illustrates a configuration example of a radiation imaging system according to a second embodiment.

Next, a second embodiment of the present invention will be described using FIG. 9 to FIG. 11. Elements in FIG. 9 to FIG. 11 that are the same as elements described in the first embodiment are assigned the same reference numerals, and detailed descriptions thereof are omitted. FIG. 9 is a block diagram illustrating a configuration example of a radiation imaging system according to the second embodiment of the present invention. FIGS. 10A and 10B are views for describing detection capability setting. FIG. 11 is a view illustrating an example of a detection capability setting table.

Hereunder, points in which the present embodiment differs from the first embodiment are described. The Present embodiment differs from the first embodiment in that a plurality of sets of the radiation detection sensor 121, the current detecting unit 122, and the comparison unit 123 are provided. A plurality of the radiation detection sensors 121 are arranged inside the region of the detection unit 101. The point that two or more of the radiation detection sensors 121 are arranged in the detection unit 101 is different from the first embodiment. At least one of the radiation detection sensors 121 is arranged at a center part in the detection unit 101 so that radiation irradiation can be reliably detected even when the irradiation region is narrowed. As shown in FIG. 3, the current detecting unit 122 and the comparison unit 123 are connected to each radiation detection sensor 121, respectively. Each comparison unit 123 outputs a radiation detection signal. The respective radiation detection signals are input to the radiation determination unit 127, and the existence and non-existence of radiation irradiation is determined. The radiation determination unit 127 determines the start of irradiation of radiation based on the radiation detection signal of a plurality of the comparison units 123.

Next, a method of setting a gain of the current detecting unit 122 and of setting the threshold voltage Vth of the comparison unit 123 according to the present embodiment will be described using FIGS. 10A and 10B. As described above, when performing radiographing, the operator sets a radiographing kind such as a radiographing site and a build of a subject before radiographing, by means of the radiographing kind setting unit 126. The point that the gain setting unit 124 sets a gain of a plurality of the radiation detection sensors 121 depending on the radiographing kind is a feature of the present embodiment.

During radiographing, a subject region at which radiation passes though the subject and a direct transmission region at which radiation does not pass though the subject exist in the detection unit 101. In a subject region, because radiation is absorbed by she subject, the radiation amount that reaches the detection unit 101 is low in comparison to a direct transmission region. Consequently, a radiation input amount to radiation detection sensors 121 arranged in a subject region is small. Therefore, the gain of a radiation detection sensor 121 that is arranged in a subject region is set to a high value. In contrast, since a radiation amount that reaches the detection unit 101 in a direct transmission region is high, a radiation input amount to radiation detection sensors 121 arranged in a direct transmission region is large. Therefore, the gain of a radiation detection sensor 121 that is arranged in a direct transmission region is set to a low value. As described above, in accordance with a radiographing kind that was set by the radiographing kind setting unit 126, the gain setting unit 124 sets a gain of the current detecting unit 122 that corresponds to the radiation detection sensor 121 that, among a plurality of the radiation detection sensors 121, is arranged in a subject region, in which a subject is present, to a large value. Further, in accordance with a radiographing kind that was set by the radiographing kind setting unit 126, the gain setting unit 124 sets a gain of the current detecting unit 122 that corresponds to the radiation detection sensor 121 that, among a plurality of the radiation detection sensors 121, is arranged in a direct transmission region, in which a subject is not present, to a small value.

As described above, when performing radiographing, first the operator sets the radiographing kind by means of the radiographing kind setting unit 126. Next, the gain setting unit 124 performs gain setting for each current detecting unit 122 based on radiographing site information from the radiographing kind setting unit 126. FIG. 10A illustrates a gain setting example for radiographing the front of the chest in a case where the radiation detection sensors 121 are arranged at nine places. When radiographing the front of the chest, there is a high possibility that the four peripheral corners will be direct transmission regions. Therefore, the gain setting unit 124 sets the gain of each current detecting unit 122 at the four peripheral corners to a low value, and sets the gain of each current detecting unit 122 at the other five places to a high value. FIG. 10B illustrates a gain setting example for radiographing a side of the chest. When radiographing the side of the chest, there is a high possibility that six places where the radiation detection sensors 121 are arranged on the left and right sides around the center region will be direct transmission regions. Therefore, the gain setting unit 124 sets the gain of each current detecting unit 122 arranged at the six places on the left and right sides around the center region to a low value, and sets the gain of each current detecting unit 122 at the other three places to a high value.

FIG. 11 illustrates an example of a gain setting table according to radiographing kinds. The gain of a direct transmission region is also set in the gain setting table. Similarly to the first embodiment, utilizing data relating to conditions for irradiation of radiation that are determined based on the radiographing site and build of the subject, she gain setting unit 124 performs gain setting with respect to the current detecting unit 122 based on an estimated radiation input amount to she radiation detection sensor 121. It is desirable for the gain setting to be set so as to be in inverse proportion to the radiation input amount. Further, the threshold voltage Vth of the comparison unit 123 may be changed according to the gain setting, or may be fixed to a voltage value that has a margin with respect to noise at all gain settings.

In the present embodiment, a radiation detection signal from the comparison unit 123 is input to the radiation determination unit 127. A plurality of radiation detection signals are input to the radiation determination unit 127, and the radiation determination unit 127 outputs a radiation irradiation determination signal to the signal processing unit 105 of the imaging apparatus 100. The signal processing unit 105 outputs a signal to the control unit 106 to stop an initializing operation and transition to an accumulation operation. As a result, the imaging apparatus 100 transitions to an accumulation operation.

Here, the radiation determination unit 127 may immediately output a radiation determination signal upon input of any one radiation detection signal, or may output the radiation determination signal after two or more radiation detection signals are input. In the former case, since the radiation detection signal that is detected earliest among radiation detection signals from a plurality of radiation detection sensors 121 is used, a time period from when radiation is irradiated until the start of irradiated of radiation is detected by the radiation detection unit 120 can be shortened compared to the first embodiment. Further, in the latter case, since two or more radiation detection signals are used, erroneous detection can be reduced to enable accurate radiation detection. As described in the foregoing, when a radiation detection signal that indicates the start of irradiation of radiation or the end of irradiation is input from any one of a plurality of the comparison units 123, the radiation determination unit 127 determines the start or end of radiation irradiation. Alternatively, when a radiation detection signal that indicates the start of irradiation of radiation or the end of irradiation is input from two or more of a plurality of the comparison units 123, the radiation determination unit 127 determines the start or end of irradiation of radiation.

Further, the start of irradiation of radiation may also be determined by the following operation. The best determination method according to the present embodiment will now be described. First, upon the input of any one radiation detection signal, the radiation determination unit 127 outputs a radiation determination signal to temporarily stop an initializing operation of the imaging apparatus 100. Thereafter, if a second radiation detection signal is input to the radiation determination unit 127, the imaging apparatus 100 transitions to an accumulation operation. If a second radiation detection signal is not input so the radiation determination unit 127, the radiation determination unit 127 determines that there was an erroneous detection and outputs a signal to the imaging apparatus 100 so as to cause the imaging apparatus 100 to resume the standby driving operation, that is, the initializing operation again. By this operation, the occurrence of erroneous detection can be decreased and to also lessen the outflow of signals from the conversion elements S11 to S33 caused by an initializing operation.

According so the present embodiment, by providing two or more radiation detection sensors 121 and also setting a detection capability in accordance with the radiographing kind, a radiation detection system can be constructed in which there are few erroneous detections and in which a time period from when radiation is irradiated until the radiation is detected is short.

Although irradiation of radiation is detected using the radiation detection sensors 121 in the present embodiment, a configuration may also be adopted in which two or more radiation detecting pixels are separately provided in the detection unit 101. In this case, similarly to the first embodiment, instead of the gain setting of the current detecting unit 122, a configuration is adopted so that the sensitivity of the two or more radiation detecting pixel can be set.

Further, in the present embodiment, radiation irradiation may also be detected by detecting a current that flows through the bias line Bs of the detection unit 101. In such case, the bias line Bs is divided into two or more regions, and the above described current detecting unit 122 and comparison unit 123 are connected to the two or more regions, respectively. A method of determining radiation irradiation in this case is the same as the method described above.

Third Embodiment

Figure 12:
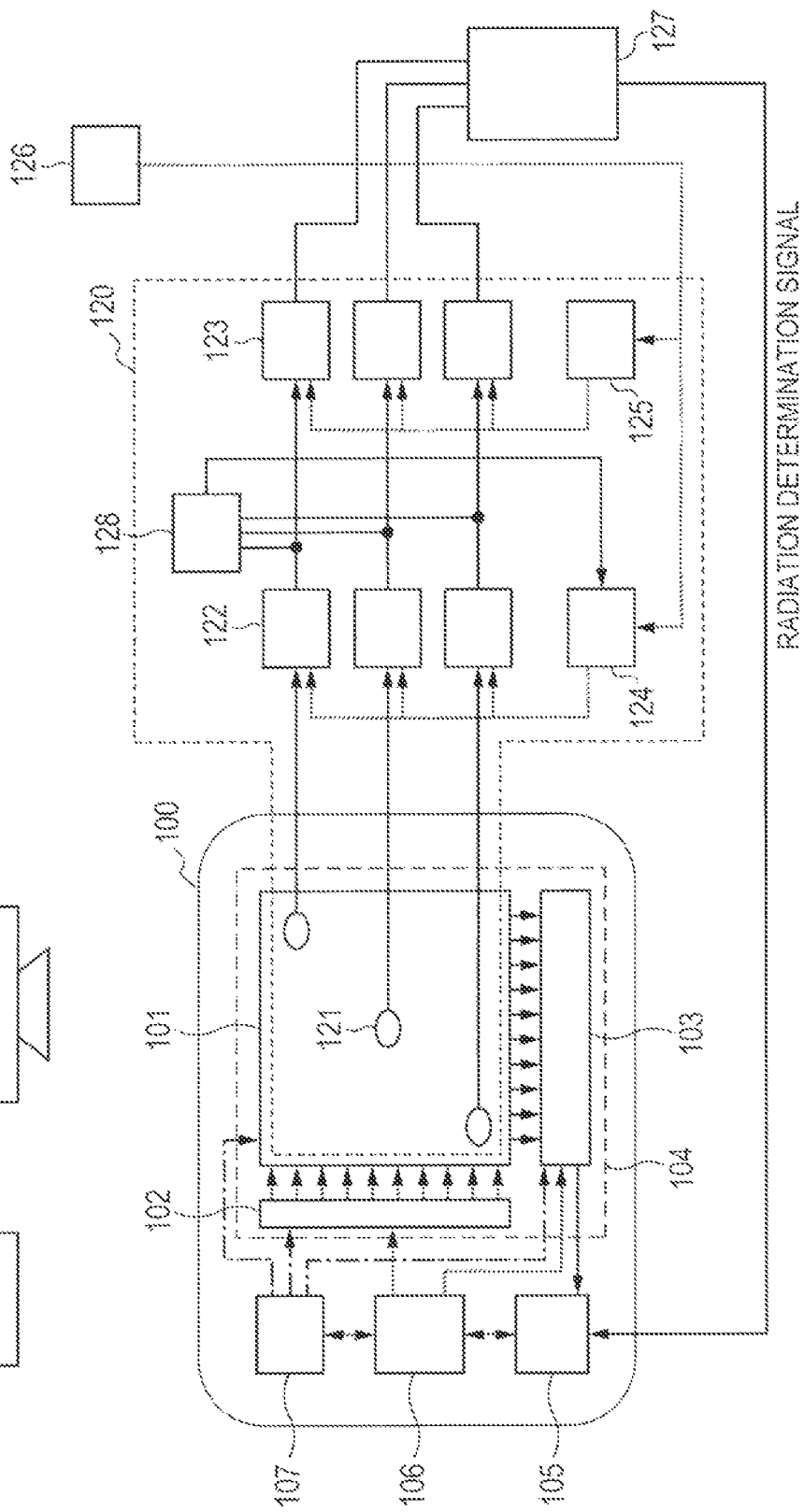
FIG. 12 is a view that illustrates a configuration example of a radiation imaging system according to a third embodiment.
Figure 13:
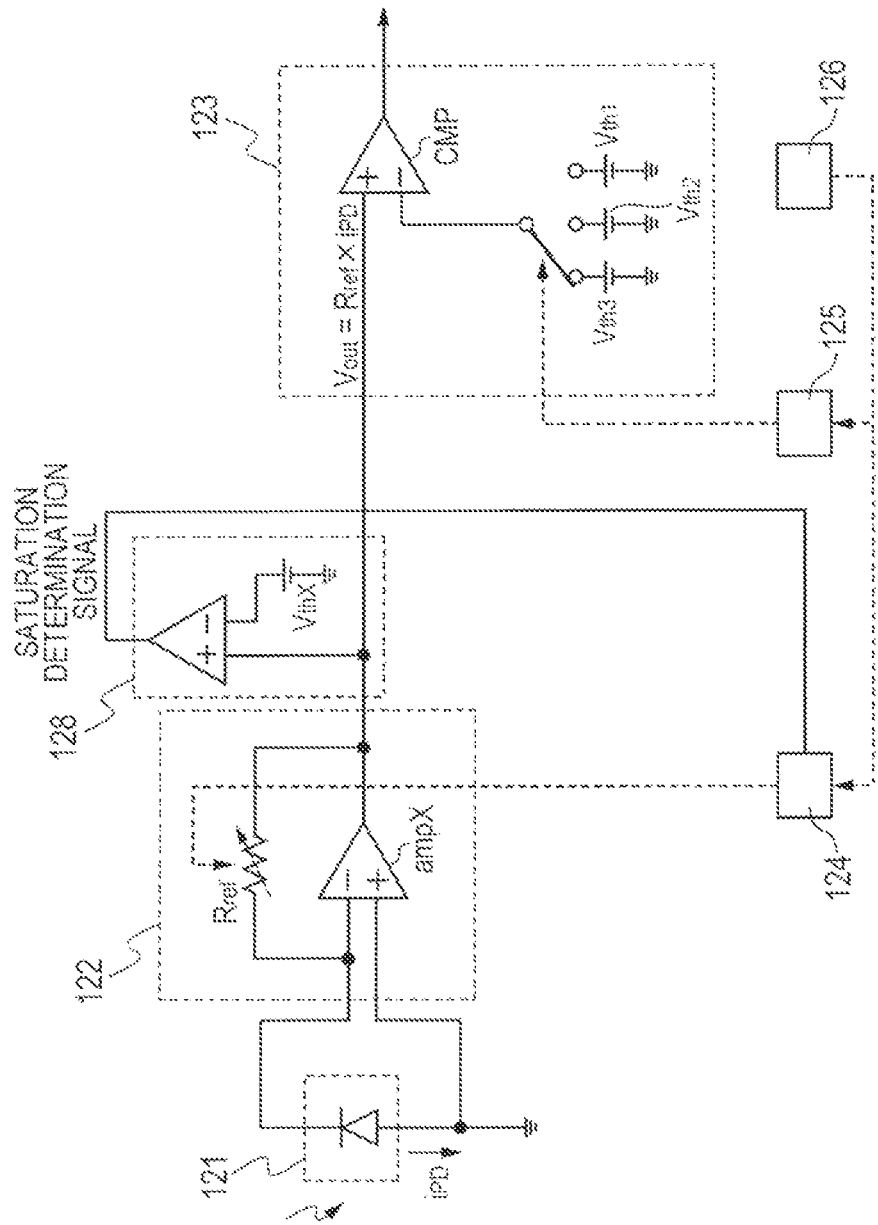
FIG. 13 is an equivalent circuit diagram of radiation detection unit.
Figure 14:
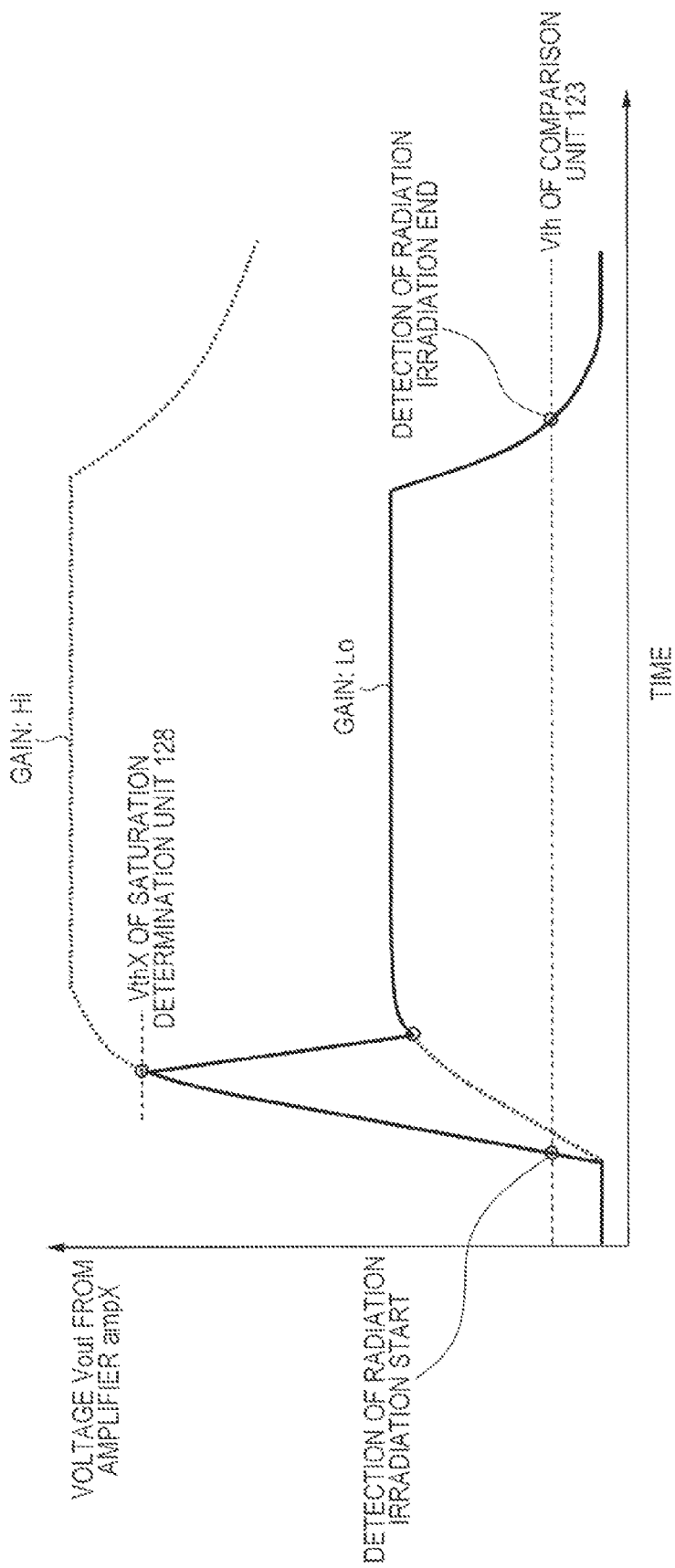
FIG. 14 is a view for describing gain setting.

Next, a third embodiment of the present invention will be described using FIGS. 12 to 14. Elements in FIGS. 12 to 14 that have the same configuration as in the second embodiment are assigned the same reference numerals, and detailed descriptions thereof are omitted. FIG. 12 is a block diagram illustrating a configuration example of a radiation imaging system according to the third embodiment of the present invention. FIG. 13 is an equivalent circuit diagram of the radiation detection unit 120. FIG. 14 is a view for describing gain setting.

Differences between the present embodiment and the second embodiment are described below. As illustrated in FIG. 12 and FIG. 13, the present embodiment is different from the second embodiment in that a saturation determination unit 128 is connected to the output of the amplifier ampX of current detecting unit 122. In the second embodiment, the detection capabilities of two or more radiation detection sensors 121 arranged in the detection unit 101 were set based on the setting of the radiographing kind setting unit 126. The gain was set to a high value at locations at which a radiation input amount to the radiation detection sensor 121 is small, while the gain was set to a low value at locations at which a radiation input amount is large. However, in actuality, there are some cases where the gain setting at the respective locations, which set based on the radiographing kind setting unit 126, is inappropriate. For example, such cases are as follows.

The location of a subject within the detection unit 101 deviates from a preset subject region.

The radiation detection sensors 121 are arranged at a boundary between a direct transmission region and a subject region.

There is an individual difference with respect to the build of the subject.

The following effects are as adverse effects in such a case. When excessively strong radiation is irradiated at the radiation detection sensor 121 for which the gain is set to a high value, the amplifier ampX inside the current detecting unit 122 saturates and no longer operates normally. When the amplifier ampX saturates, the time response deteriorates and time is taken to detect the end of radiation irradiation, and the end of irradiation can no longer be detected accurately. Therefore, according to the present embodiment, the saturation determination unit 128 is connected to the output of the amplifier ampX.

The operations of the saturation determination unit 128 will now be described using FIG. 13 and FIG. 14. The saturation determination unit 128 monitors the output voltage Vout of the amplifier ampX, and when the voltage value Vout exceeds the threshold voltage Vthx that is set to a lower voltage than the saturation voltage, the saturation determination unit 128 outputs a saturation determination signal to the gain setting unit 124. The gain setting unit 124 inputs the saturation determination signal, and lowers the resistance value of the feedback resistance Rref of the current detecting unit 122. That is, the gain setting unit 124 sets the gain to a low value. The gain setting unit 124 lowers the gain of the current detecting unit 122 if the voltage of the current detecting unit 122 exceeds a threshold voltage Vthx. By performing this operation, saturation of de amplifier ampX can be prevented, and the timing of the end of radiation irradiation can be accurately detected.

When the voltage Vout from the amplifier ampX is less than the threshold voltage Vth, the comparison unit 123 outputs a signal indicating the end of irradiation of radiation to the radiation determination unit 127. A plurality of signals indicating the end of irradiation of radiation are input to the radiation determination unit 127, and the radiation determination unit 127 outputs a radiation determination signal to the signal processing unit 105 of the imaging apparatus 100. The signal processing unit 105 outputs a signal so the control unit 106 to stop the accumulation operation and transition to a read operation. As a result, the imaging apparatus 100 transitions to a read operation.

The radiation determination unit 127 may immediately output a radiation determination signal upon input of any one signal indicating the end of irradiation of radiation, or may output the radiation determination signal after two or more signals indicating the end of irradiation of radiation are input.

In the present embodiment, in a case where gain settings at respective locations that were set based on the radiographing kind setting unit 126 are inappropriate, it is possible to avoid saturation of the amplifier ampX and to accurately detect both the start of irradiation and the end of irradiation.

Figure 15:
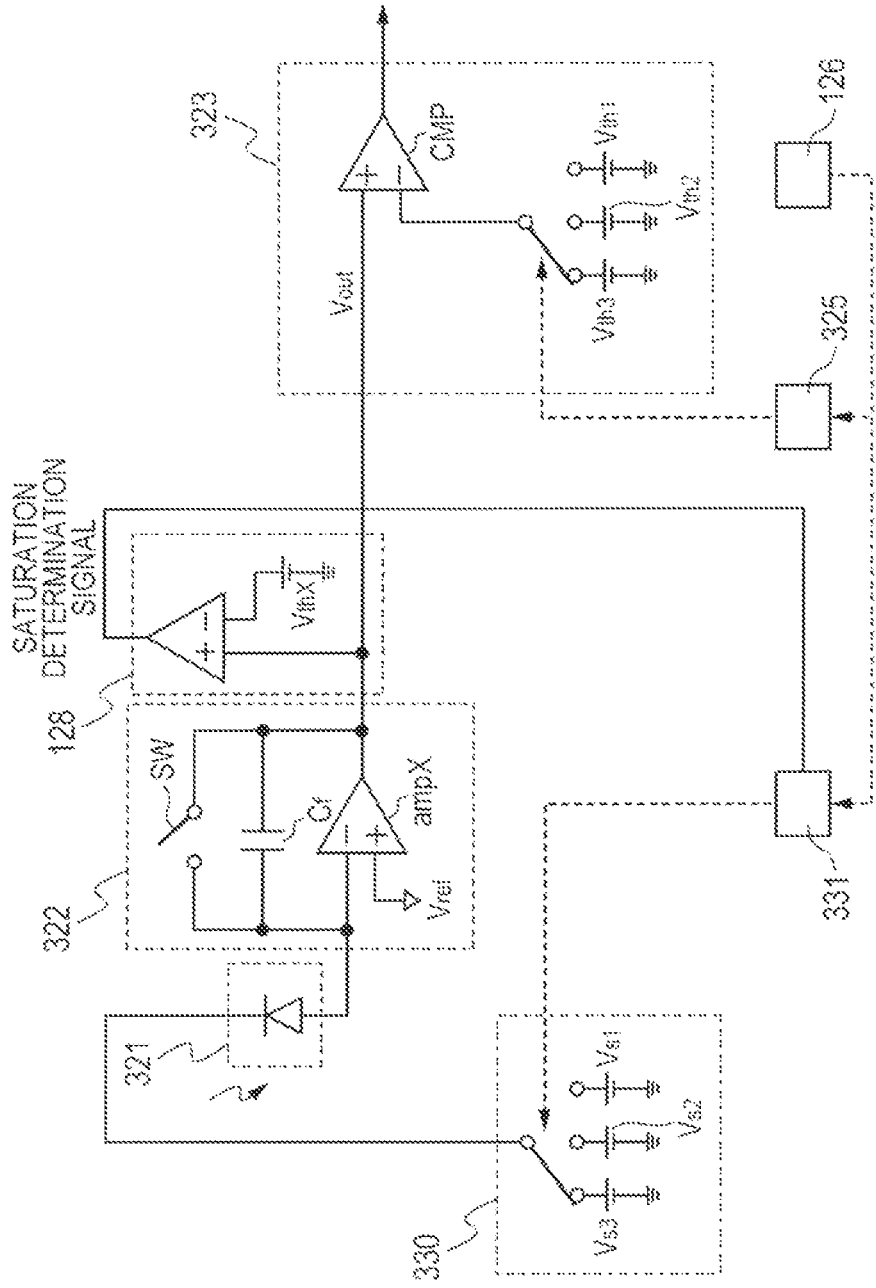
FIG. 15 is an equivalent circuit diagram of a radiation detection unit.

Similarly to the second embodiment, two or more radiation detecting pixels 321 may be separately provided in the detection unit 101. FIG. 15 is an equivalent circuit diagram of the radiation detection unit in this case. The bias switching unit 330 is provided to enable setting of the sensitivity of the two or more radiation detecting pixels 321, respectively, instead of the gain setting of the current detecting unit 122. The bias switching unit 330 supplies any one of bias voltages Vs1 to Vs3 to the radiation detecting pixel 321 according to the setting of the bias setting unit 331. The saturation determination unit 128 is connected to the output of the voltage detecting unit 322. The saturation determination unit 128 monitors the output voltage Vout of the amplifier ampX, and if the output voltage Vout exceeds the threshold voltage Vthx that is set to a lower voltage than a voltage at which the radiation detecting pixel 321 saturates, the saturation determination unit 128 outputs a saturation determination signal to the bias setting unit 331. The bias setting unit 331 inputs the saturation determination signal, and lowers the bias voltage of the bias switching unit 330. That is, the bias setting unit 331 lowers the sensitivity of the radiation detecting pixel 321. It is thereby possible to prevent the occurrence of a situation in which the radiation detecting pixel 321 saturates and the time response deteriorates.

According to the first to third embodiments, the radiation detection unit 120 changes a radiation detection capability in accordance with a radiographing kind that is set by the radiographing kind setting unit 126. Specifically, the radiation detection unit 120 increases a radiation detection capability in a case of a radiographing kind for which a radiation input amount to the radiation detection unit 120 is small, and decreases a radiation detection capability in a case of a radiographing kind for which a radiation input amount to the radiation detection unit 120 is large.

The radiation imaging systems according to the first to third embodiments are favorably used for still image radiographing like general radiographing or moving image radiographing such as fluoroscopic radiographing for medical diagnosis. Note that the term "radiation" in the above description refers not only to alpha rays, beta rays, and gamma rays which are generated by particles (including photons) emitted due to radioactive decay, but also includes beams having energy equal to or greater than the aforementioned rays, for example, X-rays, particle beams, and cosmic rays.

It is to be understood that the foregoing embodiments are intended to merely illustrate specific examples of the present invention, and are not intended to limit the technical scope of the present invention. That is, the present invention can be implemented in various forms without departing from the technical concept or the principal features thereof.

While the present invention has been described with reference exemplary embodiments, it is to be understood that the invention is not limited to the disclosed exemplary embodiments. The scope of the following claims is to be accorded the broadest interpretation so as to encompass all, such modifications and equivalent structures and functions.

This application claims the benefit of Japanese Patent Application No. 2012-192455, filed Aug. 31, 2012, which is hereby incorporated by reference herein in its entirety.

What is claimed is:

1. A radiation imaging apparatus comprising:
a detection unit in which conversion elements that convert radiation into an electric signal are arranged in a matrix shape;
a radiation detection unit configured to detect an irradiation state of radiation in accordance with a signal from a radiation detection sensor that generates the signal in response to irradiated radiation;
a drive circuit configured to drive the detection unit in accordance with the irradiation state detected by the radiation detection unit; and
a radiographing kind setting unit configured to set a radiographing kind,
wherein the radiation detection unit changes a radiation detection capability in accordance with the radiographing kind set by the radiographing kind setting unit such that the radiation detection capability is increased in a case of a radiographing kind for which a radiation input amount to the radiation detection unit is small, and the radiation detection capability is decreased in a case of a radiographing kind for which a radiation input amount to the radiation detection unit is large.

2. The radiation imaging apparatus according to claim 1, wherein:
when a start of irradiation of radiation is detected by the radiation detection unit, the drive circuit makes an operating state of the detection unit transition from a standby state to an accumulation state; and
when an end of irradiation of radiation is detected by the radiation detection unit, the drive circuit makes the operating state of the detection unit transition from the accumulation state to a read state.

3. The radiation imaging apparatus according to claim 1, wherein the radiation detection unit comprises:
the radiation detection sensor, wherein the radiation detection sensor is configured to convert irradiated radiation to a current so as to generate the signal;
a current detecting unit configured to convert the current of the radiation detection sensor to a voltage; and
a comparison unit configured to compare the voltage of the current detecting unit and a threshold voltage, output a radiation detection signal indicating a start of irradiation of radiation when the voltage of the current detecting unit exceeds the threshold voltage, and output a radiation detection signal indicating an end of irradiation of radiation when the voltage of the current detecting unit is less than the threshold voltage.

4. The radiation imaging apparatus according to claim 3, wherein the radiation detection unit further comprises a gain setting unit configured to set a gain of the current detecting unit in accordance with a radiographing kind set by the radiographing kind setting unit.

5. The radiation imaging apparatus according to claim 3, wherein the radiation detection unit further comprises a threshold setting unit configured to set a threshold voltage of the comparison unit in accordance with the radiographing kind set by the radiographing kind setting unit.

6. The radiation imaging apparatus according to claim 3, wherein the radiation detection unit comprises:

a gain setting unit configured to set a gain of the current detecting unit in accordance with the radiographing kind set by the radiographing kind setting unit; and a threshold setting unit configured to set a threshold voltage of the comparison unit in accordance with the radiographing kind set by the radiographing kind setting unit.

7. The radiation imaging apparatus according to claim 3, wherein:

a plurality of sets of the radiation detection sensor, the current detecting unit, and the comparison unit are provided;

the plurality of radiation detection sensors are arranged within a region of the detection unit; and the radiation detection unit further comprises a radiation determination unit configured to determine a start of irradiation of radiation based on a radiation detection signal of the plurality of comparison units.

8. The radiation imaging apparatus according to claim 7, wherein, in a case where the radiation detection signal indicating a start of irradiation of radiation or an end of irradiation of radiation is input from any one of the plurality of comparison units, the radiation determination unit determines a start or an end of irradiation of radiation.

9. The radiation imaging apparatus according to claim 7, wherein, in a case where the radiation detection signal indicating a start of irradiation of radiation or an end of irradiation of radiation is input from two or more of the plurality of comparison units, the radiation determination unit determines a start or an end of irradiation of radiation.

10. The radiation imaging apparatus according to claim 7, wherein the radiation determination unit comprises a gain setting unit configured to, in accordance with the radiographing kind set by the radiographing kind setting unit, set a gain of the current detecting unit that corresponds to a radiation detection sensor among the plurality of radiation detection sensors that is arranged in a subject region in which a subject is present to a large amount, and set a gain of the current detecting unit that corresponds to a radiation detection sensor among the plurality of radiation detection sensors that is arranged in a direct transmission region in which a subject is not present to a small amount.

11. The radiation imaging apparatus according to claim 4, wherein the gain setting unit lowers the gain of the current detecting unit in a case where the voltage of the current detecting unit exceeds a threshold voltage.

12. A radiation imaging system comprising:
a radiation imaging apparatus; and
a radiation generating apparatus configured to irradiate radiation,
wherein the radiation imaging apparatus comprises:
a detection unit in which conversion elements that convert radiation into an electric signal are arranged in a matrix shape;
a radiation detection unit configured to detect an irradiation state of radiation in accordance with a signal from a radiation detection sensor that generates the signal in response to irradiated radiation;
a drive circuit configured to drive the detection unit in accordance with the irradiation state detected by the radiation detection unit and
a radiographing kind setting unit configured to set a radiographing kind,
wherein the radiation detection unit changes a radiation detection capability in accordance with the radiographing kind set by the radiographing kind setting unit such that the radiation detection capability is increased in a case of a radiographing kind for which a radiation input amount to the radiation detection unit is small, and the radiation detection capability is decreased in a case of a radiographing kind for which a radiation input amount to the radiation detection unit is large.

13. A radiation imaging apparatus comprising:
a detection unit configured to output an image signal that corresponds to radiation for radiographing;
a setting unit configured to set a radiographing kind; and
a radiation detection unit configured to detect a start of irradiation of radiation in accordance with a signal from a radiation detection sensor that generates the signal in response to irradiated radiation,
wherein the radiation detection unit changes a radiation detection capability in accordance with the radiographing kind set by the setting unit such that the radiation detection capability is increased in a case of a radiographing kind for which a radiation input amount to the radiation detection unit is small, and the radiation detection capability is decreased in a case of a radiographing kind for which a radiation input amount to the radiation detection unit is large.

14. A radiation imaging system comprising:
a radiation imaging apparatus; and
a radiation generating apparatus configured to irradiate radiation.
wherein the radiation imaging apparatus comprises:
a detection unit configured to output an image signal that corresponds to radiation for radiographing;
a setting unit configured to set a radiographing kind; and
a radiation detection unit configured to detect a start of irradiation of radiation in accordance with a signal from a radiation detection sensor that generates the signal in response to irradiated radiation,
wherein the radiation detection unit changes a radiation detection capability in accordance with the radiographing kind set by the setting unit such that the radiation detection capability is increased in a case of a radiographing kind for which a radiation input amount to the radiation detection unit is small, and the radiation detection capability is decreased in a case of a radiographing kind for which a radiation input amount to the radiation detection unit is large.

15. A radiation imaging apparatus comprising:
a detection unit configured to output an image signal that corresponds to radiation for radiographing;
a setting unit configured to set one of a plurality of radiographing kinds, including first and second radiographing kinds; and
a radiation detection unit, having a radiation detection sensitivity, configured to detect a start of irradiation of radiation,
wherein a radiation input amount to the radiation detection unit is larger for the second radiographing kind than for the first radiographing kind, and
wherein the radiation detection unit changes the radiation detection sensitivity such that, when the second radiographing kind is set by the setting unit, the radiation detection sensitivity becomes smaller for the second radiographing kind than for the first radiographing kind.

16. The radiation imaging apparatus according to claim 15, wherein the radiation detection unit changes the radiation detection sensitivity such that, when the first radiographing kind is set by the setting unit, the radiation detection sensitivity becomes larger for the first radiographing kind than for the second radiographing kind.

17. The radiation imaging apparatus according to claim 15, wherein the radiation detection unit comprises:
- a radiation detection sensor configured to convert irradiated radiation to a current;
- a voltage detection unit configured to detect a voltage based on the current of the radiation detection sensor; and
- a comparison unit configured to compare the voltage of the voltage detection unit and a threshold voltage, and output a radiation detection signal indicating a start of irradiation of radiation when the voltage of the voltage detection unit exceeds the threshold voltage,
- wherein the radiation detection sensitivity comprises a sensitivity of the radiation detection sensor and a gain of the voltage detection unit.

18. The radiation imaging apparatus according to claim 17, wherein the radiation detection unit further comprises a gain setting unit configured to set the gain of the voltage detection unit in accordance with one of the plurality of radiographing kinds set by the setting unit.

19. The radiation imaging apparatus according to claim 17, wherein the radiation detection unit further comprises a threshold setting unit configured to set the threshold voltage of the comparison unit in accordance with one of the plurality of radiographing kinds set by the setting unit.

20. A radiation imaging system comprising:
- a radiation imaging apparatus; and
- a radiation generating apparatus configured to irradiate radiation, wherein the radiation imaging apparatus comprises:
- a detection unit configured to output an image signal that corresponds to radiation for radiographing;
- a setting unit configured to set one of a plurality of radiographing kinds, including first and second radiographing kinds; and
- a radiation detection unit, having a radiation detection sensitivity, configured to detect a start of irradiation of radiation,
- wherein a radiation input amount to the radiation detection unit is larger for the second radiographing kind than for the first radiographing kind, and
- wherein the radiation detection unit changes the radiation detection sensitivity such that, when the second radiographing kind is set by the setting unit, the radiation detection sensitivity becomes smaller for the second radiographing kind than for the first radiographing kind.

* * * * *